United States Patent [19]

Jen

[11] Patent Number: 5,218,858
[45] Date of Patent: Jun. 15, 1993

[54] THIN ROD FLEXURAL ACOUSTIC WAVE SENSORS

[75] Inventor: Cheng-Kuei Jen, Brossard, Canada

[73] Assignee: National Research Council of Canada, Ottawa, Canada

[21] Appl. No.: 679,604

[22] Filed: Apr. 3, 1991

[30] Foreign Application Priority Data

Apr. 4, 1990 [CA] Canada ................................. 2013859

[51] Int. Cl.$^5$ ........................ G01N 9/10; G01N 29/02; G01F 23/22
[52] U.S. Cl. ................................ 73/32 A; 73/290 V; 73/24.06; 73/61.79; 374/119
[58] Field of Search ................. 73/19.03, 24.01, 24.02, 73/24.03, 24.04, 24.05, 24.06, 32 A, 54, 41, 61.49, 597, 61.61, 61.75, 61.79, 290 V; 374/119

[56] References Cited

U.S. PATENT DOCUMENTS

| 2,536,128 | 1/1951 | Firestone et al. ...................... 73/627 |
| 3,538,750 | 11/1970 | Lynnworth ........................... 73/597 |
| 3,744,301 | 7/1973 | Arave .................................... 73/61.75 |
| 4,055,072 | 10/1977 | Fletcher et al. ..................... 73/24.01 |
| 4,248,087 | 2/1981 | Dennis et al. ...................... 73/290 V |
| 4,461,178 | 7/1984 | Chamuel ............................... 73/599 |
| 4,912,978 | 4/1990 | Solmos ................................. 73/24.03 |
| 5,042,298 | 8/1991 | Grein et al. ........................ 73/290 V |

OTHER PUBLICATIONS

"Measurement of Wire Temperature" by V. A. Johnson, Western Electric Technical Digest No. 10, Apr. 1968 pp. 25–26.
"Unified Approach to Analyse Mass Sensitivities of Acoustic Gravimetric Sensors,"Wang, et al., *Electronics Letters*, 1990, vol. 26, pp. 1511–1512.
"Analysis of Thin Rod Flexural Acoustic Wave Gravimetric Sensors," Jen, et al., *Appl. Phys. Lett.*, 1990, vol. 56, pp. 2183–2185.
"An Analysis of Thin-Rod Flexural Acoustic Wave Gravimetric Sensors Immersed in Liquid,"Jen, et al., *IEEE Trans. Ultrason. Ferroelec. Freq.* May 1991, vol. 38, pp. 312–314.
"Analysis of Thin Rod Acoustic Wave Gravimetric Sensors," Wang, et al., *Proceedings of Ultrasonics Int'l, 1990, pp. 345–349.*
"Thin Rod Flexural Acoustic Wave Devices: A Sensor Candidate," Jen, et al., *Proceedings QNDE*, 1990, vol. 10B, pp. 867–874.

*Primary Examiner*—Hezron E. Williams
*Assistant Examiner*—Rose M. Finley
*Attorney, Agent, or Firm*—Collard & Roe

[57] ABSTRACT

A flexural acoustic wave sensing method and efficient, simple, miniature and economical ultrasonic devices using thin rods are presented. The diameter of the thin rod is less than one acoustic wavelength. The lowest order flexural acoustic wave, $F_{11}$ mode, propagating along such thin rods is used. The thin rod materials can be metals, glasses, ceramics, polymers and single crystals. Any external disturbance which can alter the propagation characteristics of $F_{11}$ mode may be monitored by recording such variation. Fiber acoustic interferometers, which are built by jointing two thin rods, can offer high sensitivity. These devices are primarily used for sensors.

12 Claims, 3 Drawing Sheets

THIN ROD FLEXURAL ACOUSTIC WAVE SENSORS

FIELD OF THE INVENTION

The present invention relates generally to the acoustic wave sensing technique. More specifically, it is directed to a method and an apparatus for sensing of certain parameters using an elongated acoustic wave transmissive body in which the lowest order flexural acoustic waves are propagated.

BACKGROUND OF THE INVENTION

Integrated sensors have played an important role to the industry because they become the micro-sensing-organs for many automation processes. In the area of environment protection, reliable and cheap chemical vapor sensors are very attractive. Thus, recently the research and development of integrated acoustic sensors based on bulk and surface acoustic waves became of increasing interest. These acoustic sensors can determine concentrations of biological or chemical substances, electric and magnetic fields, temperature, and a wide range of mechanical properties such as acceleration, viscosity, etc. Most of these sensors operate in a gaseous medium, though a few are designed for use with liquids or solids.

The basic sensing mechanism of such acoustic devices is that if a parameter can alter the propagation characteristics of the acoustic waves such as velocity, amplitude or phase, then the change of the acoustic wave properties can then be correlated to the variation of this parameter. In other words, it is possible to monitor the change of this parameter by recording the acoustic property variation. In order to increase the sensitivity, differential sensing geometry is commonly adopted. This geometry requires two nearly identical acoustic wave paths, one being used as the sensing arm which is exposed to the intended measurand, and another as the reference arm. The differential output of these two arms is correlated to the variation of the measurand. The differential geometry is more reliable also as it is less sensitive to temperature and pressure variations or the like.

The operation principle of a common chemical acoustic sensor is that a coating is provided in the sensor arm of a differential acoustic sensor. This particular coating may absorb specific chemical vapor surrounding the device. The absorbed chemical vapor may increase the mass loading of the device, therefore change the properties of the propagating acoustic waves. These types of devices are called gravimetric sensors. A table below lists some examples of the coating and the measured chemical vapors or gases. A significant drawback of such sensors is that once the chemical vapor is trapped in the coating, it is very difficult to desorb it. That means that the device must be replaced after its use. It also means that the device must be disposable and cheap.

| Number | Coating | Material to be sensed |
|---|---|---|
| 1 | No | Vapor (water, acetone, methanol) |
| 2 | Triethanolamine | $SO_2$ |
| 3 | Palladium | Hydrogen |
| 4 | $WO_3$ | $H_2S$ |
| 5 | Polyethylene maleate | Cyclopentadiene |
| 6 | Phthalocyanines | $NO_2$, $NO_3$ |
| 7 | Poly(dimethyl-siloxane) | Pentane, Hexane, Iso-octane, Toluene |

Previously, many bulk, surface and Lamb (plate) acoustic wave sensor devices are developed for such gravimetric sensing purposes. Lamb wave devices are proved to have highest sensitivity.

OBJECTS OF THE INVENTION

It is therefore an object of the present invention to provide an acoustic sensor device.

It is a further object of the present invention to provide an elongated body acoustic sensor device in which the lowest order flexural acoustic wave propagates.

It is still a further object of the present invention to provide an elongated fiber acoustic interferometer sensor device in which the lowest order flexural acoustic wave propagates.

It is still a further object of the present invention to provide a differential elongated fiber acoustic delay line oscillator sensor device in which the lowest order flexural acoustic wave propagates.

SUMMARY OF THE INVENTION

Briefly stated, the present invention is directed to an elongated flexural acoustic wave sensor for measuring an environmental parameter when used with an acoustic wave measuring instrument having an acoustic wave transmitter for transmitting a flexural acoustic wave in $F_{11}$ mode (lowest order flexural acoustic rod mode) through the sensor and an acoustic wave receiver for receiving the acoustic wave being transmitted through the sensor. The sensor includes an elongated acoustic wave transmissive body which has the sizes of its cross-section in two orthogonal directions being less than one wavelength of the acoustic wave being transmitted. The body is made of a material sensitive to the environmental parameter.

The invention is further directed to an acoustic method of measuring an environmental parameter. The method includes a step of transmitting a flexural acoustic wave in $F_{11}$ mode through an elongated environmental parameter sensing body. The method further includes a step of receiving the flexural acoustic wave being transmitted to measure changes in the propagation characteristics of the flexural acoustic wave travelling through the sensing body due to the environmental parameter.

The invention is still directed further to an acoustic wave measuring instrument for measuring an environmental parameter. The instrument includes an elongated flexural acoustic wave sensor, an acoustic wave transmitter for transmitting a flexural acoustic wave in $F_{11}$ mode through the sensor and an acoustic wave receiver for receiving the acoustic wave transmitted through the sensor. The sensor comprises an elongated acoustic wave transmissive body having the sizes of its cross-section in two orthogonal directions being less than one wavelength of the acoustic wave being transmitted. The body is made of a material sensitive to the environmental parameters.

BRIEF DESCRIPTION OF THE DRAWINGS

For a more complete understanding of the present invention and for further objects and advantages thereof, reference may be made to the following description taken in conjunction with the accompanying drawings in which.

DETAILED DESCRIPTION OF THE PREFERRED EMBODIMENTS OF THE INVENTION

Figure 1:
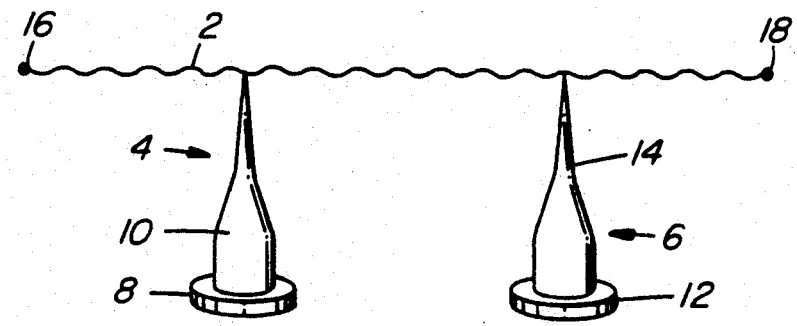
FIG. 1 shows an elongated body acoustic device according to one embodiment of the invention.

FIG. 1 illustrates schematically a basic geometry of an acoustic wave gravimetric sensing instrument, according to one of the preferred embodiments of the invention. The instrument consists of a thin elongated body such as a thin rod 2, an acoustic wave transmitter 4 and an acoustic wave receiver 6. The transmitter 4 includes an acoustic transducer 8, e.g. a piezoelectric transducer, and a glass horn 10. Similarly, the receiver includes an acoustic transducer 12, such as a piezoelectric transducer, and a glass horn 14. The transmitter generates the lowest flexural acoustic wave in $F_{11}$ mode at a spot along the thin rod to propagate the wave through it. The receiver receives the wave which has been propagated. The thin rod is fixed at both ends 16 and 18 which are provided with acoustic absorbers to ensure no acoustic wave reflections. Thin rod in this embodiment is made of a thin gold wire of 21 μm in diameter.

Figure 2:
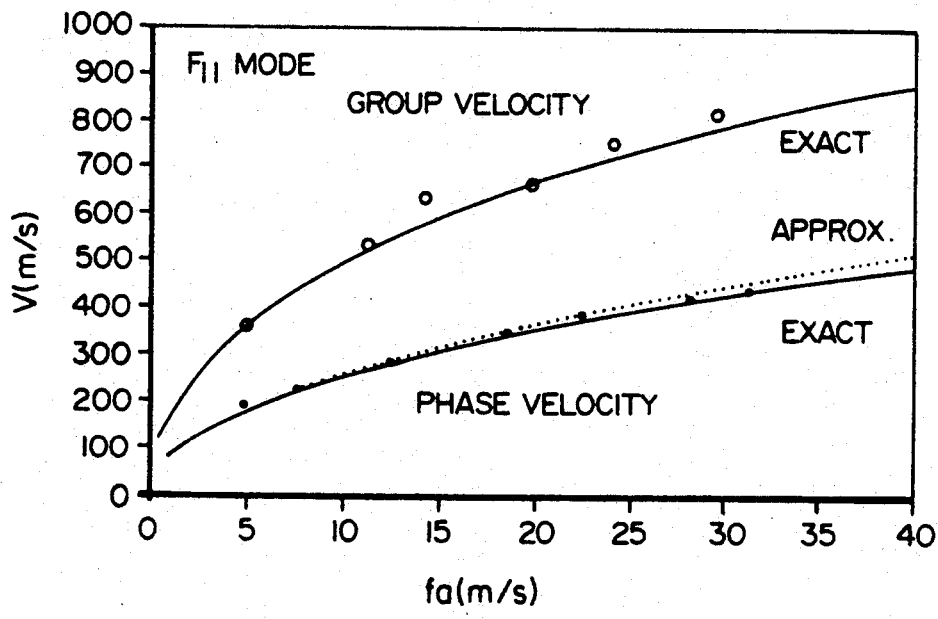
FIG. 2 shows the theoretical and measured acoustic dispersion of the lowest flexural acoustic wave, $F_{11}$ mode, propagating in a 21 μm diameter thin gold wire.

FIG. 2 is a graph which shows theoretically calculated phase and group velocities (solid lines), and measured values (open and closed circles). The vertical axis indicates the velocity V in m/s and the horizontal axis the product $fa$ of the operation frequency $f$ and the rod radius $a$ in also m/s. The graph also shows an approximation (dotted line) in addition to exact calculated values (solid lines).

One of many advantages of the gravimetric sensor according to the present invention is high mass sensitivity and this is explained below.

$$\Delta V/V_0 = S_m \Delta m_s \quad (1)$$

and $$V_0 = (\omega)^{\frac{1}{2}} a (\pi E/4m)^{\frac{1}{4}} = (\omega a/2)^{\frac{1}{2}} (E/\rho)^{\frac{1}{4}} \quad (2)$$

where $m (=\pi a^2 \rho)$ is the mass per unit length of the rod; $\Delta m_s$ is the uniformly distributed mass per unit area added to the surface of the device; E, $\rho$ and a are the Young's modulus, material density and the radius of the rod respectively. $\Delta V = (V - V_0)$; $V_0$ and V are the unloaded and loaded phased velocity respectively and $\omega$ is equal to $2\pi f$ and $f$ is the acoustic operating frequency. $S_m$ was found to be approximately $1/(2\rho a)$. The higher achievable sensitivity relies on the fact that a can be made to be very small. It also means that a rod material of low density is preferred.

An additional advantage of thin rod flexural acoustic wave devices is the very slow velocity (<1000 m/s) provided that the product of the operation frequency, $f$, and the rod radius, a, is small. The slow velocity has a merit that for instance, when the device is immersed in water, the guided $F_{11}$ mode will not leak its energy significantly into the water.

Figure 3:
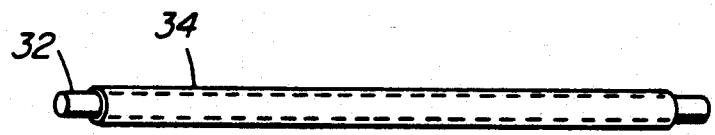
FIG. 3 shows a vapor absorptive coating on a thin rod, as another embodiment.

FIG. 3 illustrates a gravimetric sensor according to another embodiment of the invention. In this embodiment, the sensor is made of a thin rod 32 on which is provided a thin coating 34 of a material sensitive to environmental parameter. The cross-section of the aggregate must be less than one wavelength of the acoustic wave being transmitted.

The operation principle of this device is that the coating absorbs an environmental parameter, e.g. specific chemical vapor surrounding the device. Some examples of the coatings and materials to be sensed are listed in the table described previously. The absorbed chemical vapor may increase the mass loading of the device, therefore change the propagation properties of $F_{11}$ mode. One advantage of the present invention is that the thin rod may be made entirely of an absorptive material for sensing a specific chemical vapor, thus a high sensitivity can be achieved.

Several benefits are realized when the rod is less than a few wavelengths:

1) The fabrication of the rod is easy. The total amount of material required for the rod and its weight is very small.
2) It can be excited by many different types of transducers.
3) $F_{11}$ mode may have phase velocities of only 200 m/s or less (see FIG. 2), permitting thin rod vapor sensors to operate at relatively low frequency range (a few MHz), and even to operate while immersed in liquids for chemical sensing without severe wave attenuation.
4) For a given wavelength, the modes are at very different frequencies, permitting single ($F_{11}$) mode excitation.
5) For vapor sensors, the thin rod can be entirely made of a good absorptive material for a specific chemical vapor, therefore high sensitivity can be achieved.

Figure 4:
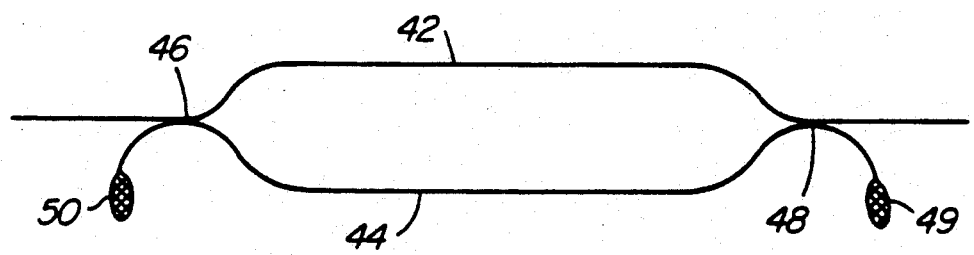
FIG. 4 shows a fiber acoustic Mach-Zehnder interferometer as still another embodiment.

In order to increase the sensitivity further, the differential sensing geometry can be used. FIG. 4 shows one of such geometries, commonly known as Mach-Zehnder interferometer. In the figure, a pair of nearly identical sensors, e.g. acoustic fibers, are coupled at two spaced-apart locations forming a sensing arm 42 and a reference arm 44. Acoustic couplers 46 and 48 form such couplings. The first coupler 46, acting as an acoustic splitter, is used to split properly the acoustic power into two fiber arms. The second coupler 48, acting as an acoustic coupler, is to join the acoustic power coming from the two fiber arms. Acoustic absorbers 49 and 50 are provided at the ends of an acoustic fiber. A flexural acoustic wave in $F_{11}$ mode is propagated through the interferometer. The transmitter and the receiver can be the same as those shown in FIG. 1. The sensing arm 42 is exposed to the intended measurand. The differential output of these two arms is correlated to the variation of the measurand. Assume the fiber couplers shown in the figure equally split and combine the acoustic power with respect to two arms. If the signal coming from the reference arm is $(A/2)\sin(\omega t + \Delta\phi)$, the output of the interferometer receiver can be expressed as:

$$S(t)=(A/2)\sin(\omega t)+(A/2)\sin(\omega t+\Delta\phi)=A\cos(\Delta\phi/2)\sin[(2\omega t+\Delta\phi)/2] \quad (3)$$

where $\Delta\phi$ is the phase change of the $F_{11}$ mode in the sensing arm due to external disturbances such as temperature variations. A is the amplitude of the acoustic signal coming from the transmitter. Again, $\omega$ is equal to $2\pi f$ and $f$ is the acoustic operating frequency. In equation (3), $A\cos(\Delta\phi/2)$ represents the signal envelope and $\sin[(2\omega t+\Delta\phi)/2]$ is the signal carrier. If the phase of the acoustic wave in the reference arm is adjusted to be 180° out of phase with respect to that in the sensing arm under no external disturbance, then the signal envelope will become $A\sin(\Delta\phi/2)$. When $\Delta\phi$ is very small, the envelope of S(t) is $\sim A\Delta\phi/2$.

For gravimetric sensors, the sensing arm sensor may be coated with a material sensitive to the measurand as shown in FIG. 3. If the sensors are of metallic wires, they can be joined at two locations by soldering, to form an interferometer. If the sensors are made of glasses or polymers, they may be fused together by any known technique.

Figure 5A:
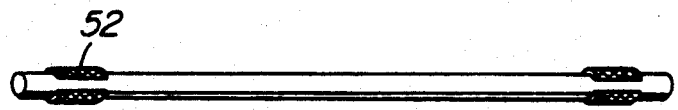
FIGS. 5a and 5b show two different electrode patterns to excite flexural acoustic waves.
Figure 5B:
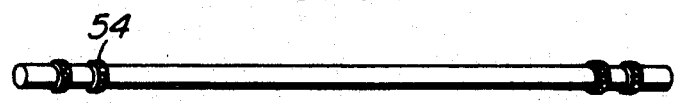

A thin rod of the sensor can be made of piezoelectric single crystal fibers such as lithium niobate or piezoelectric thin film such as zinc oxide or lead-zirconate-titanate coated rods. Then, the excitation and receiving can be achieved by simply depositing proper electrode patterns, e.g. 52 and 54, on the rods as shown in FIGS. 5a and 5b.

Figure 6A:
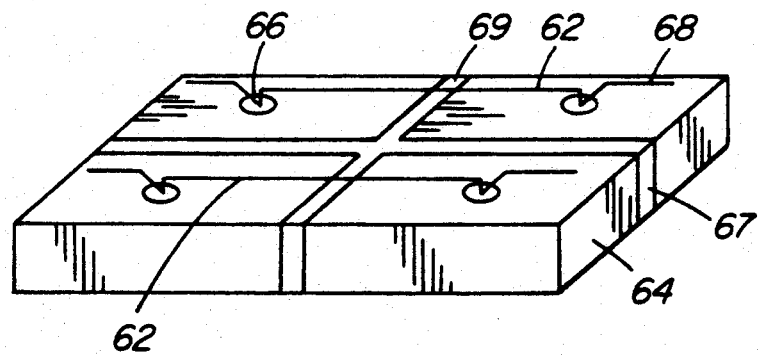
FIGS. 6a and 6b show a further embodiment of an integrated thin rod flexural acoustic wave dual delay line configuration.
Figure 6B:
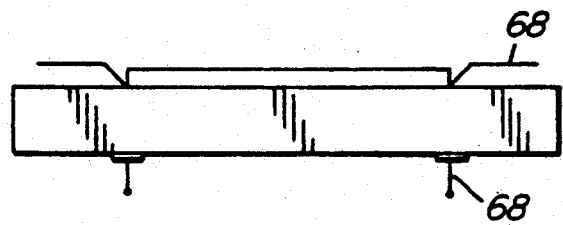
Figure 7:
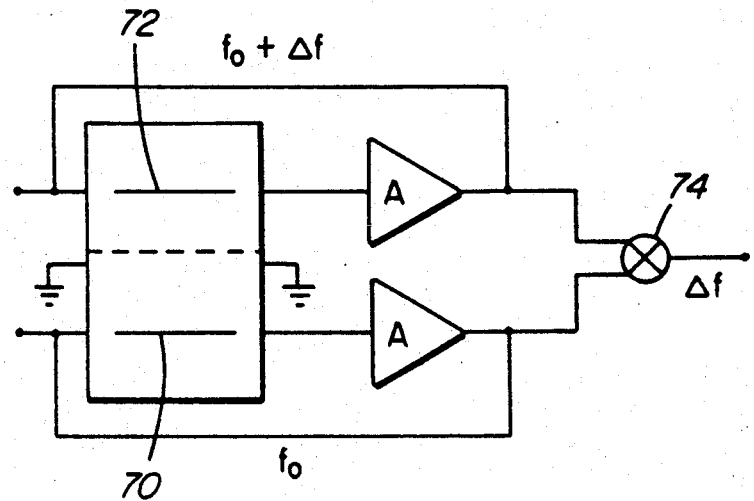
FIG. 7 illustrates a differential delay line oscillator.

As a further embodiment, an acoustic delay line can be fabricated employing the principle of the present invention. The delay lines using thin rod flexural acoustic wave can be made, according to the present invention, by the standard IC technology. They can be miniature-sized, mass produced with high reproducibility and economically fabricated. FIGS. 6a and 6b respectively show a perspective and a side view of a dual thin rod flexural acoustic delay line. A pair of rods 62, each similar to the sensor shown in FIG. 1, are provided on a piezoelectric substrate 64 by way of supports 66 such as glass horns. Electrodes 68 are also connected to the piezoelectric substrates whose material can be lithium mobate, gallium arsenide, lead zinconate titanate, a lithium titanate and quartz crystals. The substrate is divided into sections by acoustic absorber layers 67 and 69. The delay line structure shown in FIGS. 6a and 6b is used in a configuration of FIG. 7 to form a differential thin rod delay line oscillator sensor geometry. One delay line oscillator with center frequency $f_0$ is used as the reference arm 70 and another one with oscillating frequency, $f_0 + \Delta f$, is used as the probe arm 72. $\Delta f$ caused by the disturbance of the measurand can be obtained by using a frequency mixer 74 shown in FIG. 7. $\Delta f$ can be used to monitor the variation of the measurand.

The requirements of the thin rod delay line oscillator are:

$$A(\text{gain of amplifier}) \geq IL(\text{insertion loss of the delay line}) \quad (4)$$

$$\phi_{DL}\text{ (Delay Line)} + \phi_A + 2\phi_{tr} = -2n\pi \quad (5)$$

and with $$\phi_{DL} = -2\pi f_0 \tau \quad (6)$$

Hence $$f_0 = \frac{2n\pi + \phi_A + 2\phi_{tr}}{2\pi\tau} \quad (7)$$

where $\phi_A$ is the phase shift introduced by the amplifier and $2\phi_{tr}$ is the sum of the phase shifts introduced by the two identical transducers. The phase shift introduced by each transducer is determined by the transducer impedance and its load. The equation for $f_0$ shows that the oscillation frequency is inversely proportional to the acoustic signal delay, $\tau(=1/V_0)$, and therefore the change of $\tau$ can be used as a measure for thin rod delay line sensor. It also shows that the influence of $\phi_{tr}$ and $\phi_A$ can be minimized by choosing $\phi_{DL}$ large. One method is to use a long delay line (large l) at the cost of an increase of insertion loss. An alternative is to make $fa$ smaller, thus lower $V_0$. It is noted that by making a smaller, higher $S_m$ can be obtained.

Let $\phi_{DL}\omega l/V_0 > (\phi_A + 2\phi_{tr})$ and then equation (6) can be approximated by:

$$f_0 = n(V_0/l) \quad (8)$$

Figure 8:
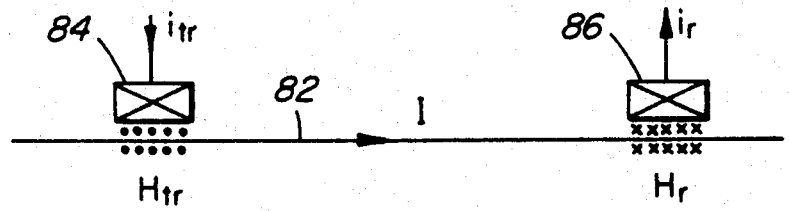
FIG. 8 shows an electromagnetic type of acoustic transducer to excite and receive the flexural acoustic waves along the thin electrically conductive body.

FIG. 8 illustrates a further embodiment using the electromagnetic type of acoustic transducer where the thin rod is a conductor. An electric DC current I flows through the thin rod 82. At the transmitter end, a magnetic field generator 84 is used to generate a magnetic field $H_{tr}$ by an AC current $i_{tr}$.

The direction of I and $H_{tr}$ is perpendicular. According to the Lorentz Law, a force, F, can be generated between these two wires and $$F = \mu_0 I L H_{tr} \quad (9)$$

where L is the interaction length and $\mu_0$ is the permeability in vacuum. If the transmitter and the receiver conductors are very heavy and fixed in their positions, then such force can displace the very light-weight thin rod, thus generate the flexural acoustic waves therein. Reciprocally at the receiver end, the displacement of the thin rod represents a force. Still due to the Lorentz Law, a small variation of $H_r$ will be generated. $H_r$ can be detected by the receiving magnetic field receiver 86, and induces an AC current, $i_r$, at the receiver end. The timing, amplitude and phase of the current, $i_r$, will be related to the acoustic properties of $F_{11}$ mode. By using this electromagnetic transreceiving mechanism, the rod does not contact with the transducers, therefore the replacement of thin rod after the chemical vapor sensing is very handy.

Figure 9:
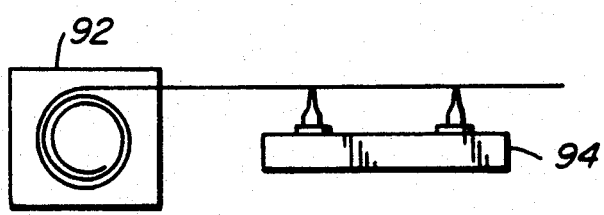
FIG. 9 is a further embodiment of the invention.

FIG. 9 is another embodiment wherein the disposability of the sensor is greatly enhanced. A container 92 houses a substantial length of the sensor out of which any required length can be reeled out and placed over the acoustic instrument 94. After use, the portion can be cut off.

I claim:

1. An elongated flexural acoustic wave sensor for measuring an environmental parameter when used with an acoustic wave measuring instrument having an acoustic wave transmitter for transmitting a flexural acoustic wave in $F_{11}$ mode through the sensor and an acoustic wave receiver for receiving the acoustic wave being transmitted therethrough, comprising:

an elongated acoustic wave transmissive body having its cross-section being less than one wavelength of the acoustic wave in $F_{11}$ mode being transmitted, said body being made of a material, where said material has at least one acoustic wave propagation characteristic that is variable with the environmental parameter.

2. The elongated flexural acoustic wave sensor, according to claim 1, wherein:

said elongated acoustic wave transmissive body being made of an elongated substrate and a thin layer of coating provided thereon, said coating being made of a material, where said coating has at least one acoustic wave propagation characteristic that is variable with the environmental parameter.

3. The elongated flexural acoustic wave sensor, according to claim 2, wherein:

said elongated substrate is made of a piezoelectric material and has a plurality of electrodes provided therein.

4. The elongated flexural acoustic wave sensor, according to claim 1, further comprising:

a container containing a substantial length of said acoustic wave transmissive body, a fraction of which is used as a sensor.

5. An acoustic wave measuring instrument for measuring an environmental, parameter, comprising:

an elongated flexural acoustic wave sensor;
an acoustic wave transmitter for transmitting a flexural acoustic wave in $F_{11}$ mode through said sensor; and
an acoustic wave receiver for receiving the acoustic wave being transmitted therethrough; in that, said sensor comprises:
a first elongated acoustic wave transmissive body having a cross-section being less than one wavelength of the acoustic wave being transmitted, said body being made of a material, where said coating has at least one acoustic wave propagation characteristic that is variable with the environmental parameter.

6. The acoustic wave measuring instrument for measuring an environmental parameter, according to claim 5, wherein said sensor further comprises:

a second elongated acoustic wave transmissive body that is substantially identical to said first transmissive body, said first and second transmissive bodies being acoustically coupled together at two spaced-apart locations along said transmissive bodies, each of said bodies having a cross-section being less than one wavelength of the acoustic wave being transmitted and at least one of said transmissive bodies being made of a material with at least one acoustic wave propagation characteristic that is variable with the environment.

7. The acoustic wave measuring instrument for measuring an environmental parameter, according to claim 5, wherein:

the elongated acoustic wave transmissive body is made of an electrically conductive material; and
said transmitter and said receiver each has an electromagnetic coil to convert an alternating current in said coil into the flexural acoustic wave in $F_{11}$ mode in said electrically conductive material and vice versa.

8. The acoustic wave measuring instrument for measuring an environmental parameter, according to claim 5, wherein:

said acoustic wave transmissive body is made of an elongated substrate and a thin layer of coating provided thereon, said coating being made of a material, said material having at least one acoustic wave propagation characteristic that is variable with the environmental parameter.

9. The acoustic wave measuring instrument for measuring an environmental parameter, according to claim 6, wherein:

each of said acoustic wave transmissive bodies is made of an elongated substrate and a thin layer of coating provided thereon, one of said coatings being made of a material, said material having at least one acoustic wave propagation characteristic that is variable with the environmental parameter.

10. The acoustic wave measuring instrument for measuring an environmental parameter, according to claim 7, wherein:

said electrically conductive material has a thin layer of coating thereon, said coating being made of a material having at least one acoustic wave propagation characteristic that is variable with the environmental parameter.

11. The acoustic wave measuring instrument for measuring an environmental parameter, according to claim 5, further comprising:

a piezoelectric substrate which is divided into four segments;
a pair of substantially identical elongated flexural acoustic wave sensors positioned in parallel with one another on said piezoelectric substrate, each of said wave sensors being acoustically connected at two spaced-apart locations to respective segments of said piezoelectric substrate; and
electrodes on said piezoelectric substrate so that when energized, the flexural acoustic waves in $F_{11}$ mode are transmitted through said sensors.

12. An acoustic wave method of measuring an environmental parameter comprising the steps of:

transmitting a flexural acoustic wave in $F_{11}$ mode through an elongated environmental parameter sensing body, said body having a cross-section less than one wavelength of the acoustic wave being transmitted; and
receiving the flexural acoustic wave being transmitted to measure changes in the propagation characteristics of the flexural acoustic wave travelling through said sensing body due to the environmental parameter.

* * * * *